United States Patent [19]  
Kuhlmey

[11] 3,992,364  
[45] Nov. 16, 1976

[54] PHYSIOLOGICALLY ACTIVE POLYPEPTIDE PREPARATION

[76] Inventor: Walter Kuhlmey, Heerstrasse 55, 28 Bremen, Schwachhauser, Germany

[22] Filed: Dec. 2, 1975

[21] Appl. No.: 637,022

Related U.S. Application Data

[63] Continuation-in-part of Ser. No. 146,523, May 24, 1971, abandoned, which is a continuation of Ser. No. 622,009, Feb. 21, 1967, abandoned.

[30] Foreign Application Priority Data

Feb. 22, 1966 United Kingdom............... 7753/66

[52] U.S. Cl. .............................. 260/112 R; 195/29
[51] Int. Cl.² ........................................ C07G 7/026
[58] Field of Search................... 195/29; 260/112 R; 424/95

[56] References Cited
UNITED STATES PATENTS 2,171,320  8/1939  Lautenschlager et al............ 424/85
3,034,963  5/1962  Wachtel............................ 424/109
3,498,964  3/1970  Hayashi............................ 195/29 X

*Primary Examiner*—Lionel M. Shapiro
*Attorney, Agent, or Firm*—Hill, Gross, Simpson, Van Santen, Steadman, Chiara & Simpson

[57] ABSTRACT

A physiologically active polypeptide effective for decreasing cholesterol levels and increasing 17 ketosteroid elimination of human patients is prepared by enzymatic proteolysis at temperatures not above 45° C of mammalian organs rich in reticulo-endotelial tissue. The polypeptide has a molecular weight of less than 5,000, an isoelectric point at pH 5.5 and an Rf value between 0.5 and 0.6 in Partridge solution. It may be administered orally or parenterally.

7 Claims, No Drawings

PHYSIOLOGICALLY ACTIVE POLYPEPTIDE PREPARATION

RELATED APPLICATIONS

This application is a continuation-in-part of the pending Walter Kuhlmey U.S. Pat. application Ser. No. 146,523, filed May 24, 1971, now abandoned, which, in turn is a continuation of the Walter Kuhlmey U.S. Pat. application Ser. No. 622,009, filed Feb. 21, 1967, now abandoned, and claiming priority of Feb. 22, 1966, under 35 USC Sec. 119, based on British Pat. application Ser. No. 7753/66, filed Feb. 22, 1966.

FIELD OF THE INVENTION

This invention relates to the preparation of a physiologically active polypeptide suitable for decreasing the cholesterol levels and increasing the 17 keto-steroid elimination of human patients, which is derived from enzymatic proteolysis of the organs of mammals which are rich in reticulo-endothelial tissue. Specifically, animal spleens, lymph glands, bone marrow and the like sources of reticulo-endothelial tissue are subject to low temperature proteolysis with pepsin, trypsin or papain, the reaction mixture is separated from the insoluble components and the resulting polypeptide separated from the filtrate by precipitation, ether extraction or the like. The precipitate solids can be formed into tablets or dragées for oral administration. The extract solutions can be administered parenterally. The low temperature prevents the proteolysis from progressing to amino acid and the active polypeptide has a molecular weight less than 5,000, behaves like a pure polypeptide in chromatography and in paper electrophoresis, has a isoletric point at pH 5.5 and an Rf value between 0.5 to 0.6 in Partridge solution.

PRIOR ART

The Lautenschlager et al U.S. Pat. No. 2,171,320 discloses a process of obtaining an anti-toxin by extracting autolysed spleen and liver with water, low molecular weight aliphatic organic solvents and mixtures of the solvents with water and then treats the solutions with heavy metal compounds. The proteolysis of the spleen and liver is an uncontrolled process and does not involve the addition of proteolytic enzymes. The resulting anti-toxin is soluble in methanol and is ineffective in lowering cholesterol levels or increasing 17 keto-steroid elimination in patients.

The Wachtel U.S. Pat. No. 3,034,963 discloses the preparation of a blood cholesterol reducing substance from the anterior and posterior lobes of the pituitary gland, the liver and brain by an extraction with an organic solvent, removing the solvent adding chloroform to the residue and passing a petroleum ether solution of the chloroform insoluble material through a chromatographic column to separate the cholesterol lowering substance from blood phospholipid lowering substances. The process does not involve enzymatic proteolysis to develop a polypeptide.

SUMMARY OF THE INVENTION

According to this invention, organs rich in reticulo-endotelial tissues are subjected to a complete enzymatic proteolysis at a temperature of not more than 45° C, the reaction mixture is separated from its insoluble components, and the polypeptide produced by the proteolysis is separated by a polypeptide separation procedure. The proteolysis is preferably carried out with pepsin, trypsin, papain and does not progress to amino acid, but remains at the short-chained, biologically active polypeptide of this invention. In contrast with long chain high molecular polypeptides the polypeptides of this invention are not further broken down by trypsin and papain and are suitable for oral administration whereas the high molecular polypeptides decompose in the stomach.

The physiologically active polypeptide produced according to this invention consists of 17 amino acids and is suited for parenteral and oral administration. In addition, the polypeptide can contain an additional prosthetic group.

If the polypeptide produced according to the inventive method undergoes hydrolysis, the following amino acids are freed. Micromoles of amino acid per 10 mg. are indicated in parenthesis following each amino acid:

| | |
|---|---|
| Lysine | (5.18) |
| Histidine | (3.28) |
| Arginene | (4.35) |
| Asparagine acid | (4.15) |
| Threonine | (5.15) |
| Serine | (3.29) |
| Glutamic acid | (6.10) |
| Proline | (6.54) |
| Glycine | (6.69) |
| Alanine | (5.85) |
| Cysteine | (0.92) |
| Valine | (5.56) |
| Methionine | (0.70) |
| Isoleucine | (2.87) |
| Leucine | (6.02) |
| Tryosine | (2.46) |
| Phenylalanine | (4.27) |

The molecular weight of the polypeptide of this invention is less than 5,000. This physiologically active polypeptide behaves like a pure polypeptide in chromatography as well as in paper electrophoresis. The isoelectric point is at pH 5.5. The Rf value of the polypeptide is between 0.5 and 0.6 in Partridge solution. The specific metabolic effect of the polypeptide consists in a decrease in the cholesterol level of the blood, as well as in an increase of 17 keto-steroid elimination.

The polypeptide of this invention is defined by its aforementioned physico-chemical data and its pharmacological features.

The polypeptide produced according to the invention is particularly suited to lowering the cholesterol level in human blood, which, particularly in the case of older persons, is very often too high, and thus can lead to arterial sclerosis. It was found that, as a result of oral use of 100 mg. daily of this polypeptide, the cholesterol level of a great number of persons could be lowered on the average by approximately 10 – 15%. The great advantage in the use of this polypeptide for lowering the cholesterol level thus consists in that the polypeptide in question is a substance which is low in toxic elements, and has a great therapeutic range while the known remedies used for lowering the cholesterol level can often lead to undesirable side effects.

It is then an object of this invention to produce a physiologically active polypeptide capable of decreasing cholesterol levels and increasing the 17 keto-steroid elimination of human patients by low temperature enzymatic proteolysis of reticulo-endotelial tissue.

Another object of this invention is to produce a low molecular weight short-chained polypeptide by low temperature enzymatic proteolysis of reticul-endotelial tissue which is effective to decrease cholesterol levels in the blood.

A specific object of the invention is to prepare a physiologically active polypeptide from animal spleens, lumph glands, bone marrow and the like sources of reticulo-endotelial tissue by enzymatic proteolysis at temperatures not above 45° C with pepsin, or trypsin or papain, separating the reaction mixture from the insoluble components and then separating the resulting polypeptide by known separation methods such as precipitation or extraction.

Other and further objects of this invention will become skilled to those in this art from the following detailed description including preferred examples of the process.

EXAMPLE 1

Bovine spleen, obtained from a slaughter house within 2 to 3 hours of the animal's death is freed from fascia and fat and stored in a deep freeze at about −18° C until it is to be used. Alternatively, the fresh spleen can be directly used without freezing. On the day of preparation, about 100 kg. of frozen spleens are allowed to thaw sufficiently for introduction into an electric mincing machine. The effluent from this machine has the consistency of finely chopped meat. The chopped spleen is transferred to a 250 liter kettle equipped with stirrer. About 120 liters of distilled water are added to the kettle, and the mixture is stirred as 25% aqueous hydrochloric solution is added until the pH of the mixture is 2.0. Then 100 grams of purified pepsin concentrate are added and the preparation is stirred for 5 hours at 40° C. It is then poured on numerous filtering funnels (about 70 are useful to accept the batch) where it is filtered without suction through linen filters. The filtrates are collected forming a volume of about 150 liters. The digested tissue is discarded.

To remove the peptide from the aqueous filtrate, 40 liters of purified phenol are added, the preparation is stirred vigorously to insure good mixture of the phases and the preparation is then allowed to separate. The phenol phase is retained and extracted repeatedly with ether serving to remove the phenol leaving an aqueous phase that contains the polypeptide which is suitable for parenteral use in this form.

EXAMPLE 2

Five kg. fresh, finely chopped beef spleen were subjected to proteolysis at 40° C for 24 hours with 5 g. pepsin 1: 1000;* whereby 5 liters distilled water were added, and the pH value of the solution was adjusted at 1.7 to 1.9 with hydrochloric acid. The reaction mixture was then subsequently filtered through a paper filter. To the clear-filtered solution, 32% by weight sodium chloride was added. The precipitate thus formed was separated and dried and was then suitable for oral administration, preferably in the form of tablets or dragées.

* (i.e. pepsin in such concentration that it is able to digest chicken albumin in an amount of thousand times its one weight).

EXAMPLE 3

Five kg. beef lymph glands were subjected to proteolysis at 40° C for 72 hours with 10 grams pepsin 1:1000; whereby 5 liters distilled water were added and the PH value of the solution was adjusted to 1.7 with hydochloric acid. The reaction mixture was then subsequently centrifuged. To the clear solution, 20 to 25% by weight phenol was added. The phenol phase was separated from the water phase in the separating funnel, and the phenol was extracted from the phenol phase by ether. The remaining concentrate, which contains the physiologically active polypeptide, was then suitable for parenteral use in this form. For the purpose of additional purification, however, the entire concentrate which was obtained from the phenol phase by removal of the phenol was diluted with water to a dry weight of 10%. The pH value of this mixture was adjusted by the addition of 7.472 g. NaH$_2$PO$_4$ and 0.784 Na$_2$HPO — 2 H$_2$O, to that of suitable buffer solution, namely 4,5, whereupon the resulting precipitate was removed by filtration or centrifuging. Upon isotonic adjustment the purified concentrate was suitable for parenteral use.

EXAMPLE 4

Five kg. fresh finely chopped pig spleen were broken down (digested) by 125 g. trypsin (1g = 40,000 fluid-gross-units) at 45° C and at a pH value of 8,0 for 6 hours; whereby 5 liters distilled water were added, and the adjustment of the pH value was to 4,5 effected by sodium hydroxide solution. The additional concentration proceeded as in Example 2.

EXAMPLE 5

Five kg. fresh, finely chopped beef spleen were treated with 40 grams raw (crude) papain at 45° C for 10 hours; whereby 5 liters distilled water were added and the pH value of the solution was adjusted to a value of 7.0 with sodium hydroxide solution. The additional concentration and purification of the mixture proceeded as in Example 3.

EXAMPLE 6

Five kg. beef bone marrow were subjected to proteolysis with 10 g pepsin at 40° C for 72 hours, whereby 5 liters distilled water were added, and the pH valve of the solution was adjusted to 1.7 with hydrochloric acid. After the concentration process through phenol extraction, as in Example 3, the concentrate was purified by means of column chromatography.

The following Tables I through III show clinical test results for lowering the cholesterol levels of patients given daily oral dosages of 100 mg. of the polypeptide of this invention for the indicated length of time. The dosages were administered orally in the amount of 100 mg. of the polypeptide produced according to Example 1.

TABLE 1

| Sex | Name | Illness | Cholesterol Level Prior to Treatment | After a One-Month Treatment |
|---|---|---|---|---|
| F | M.Be. | Coronary Insufficiency | 363 | 327 |
| F | F.Bu. | No Illness | 240 | 240 |
| M | R.As. | Bronchial Asthma | 287 | 249 |
| F | E.As. | No Illness | 250 | 245 |
| M | O.En. | Cerebral Sclerosis Arterial Sclerosis of the Leg Arteries | 219 | 214 |
| F | A.Fi. | No Illness | 278 | 274 |
| M | W.Fr., | Heart-Muscle Damage | 212 | 171 |
| F | L.Co. | Arterial Sclerosis | 248 | 220 |
| F | M.Gr. | Overfunction of the Thyroid Gland | 419 | 401 |
| F | I.Ma. | Arterial Sclerosis | 334 | 247 |
| F | R.He. | Arterial Sclerosis | 339 | 341 |

TABLE I-continued

| Sex | Name | Illness | Cholesterol Level Prior to Treatment | After a One-Month Treatment |
|---|---|---|---|---|
| M | M.Gr. | No Illness | 255 | 271 |

Significance: 98% (2d=0.02) average decrease approximately 16%

TABLE II

| Sex | Name | Illness | Cholesterol Level Prior to Treatment | After a Two-Month Treatment |
|---|---|---|---|---|
| F | M.Be. | Coronary Insufficiency | 363 | 332 |
| M | F.Bl. | No Illness | 280 | 210 |
| M | H.Br. | Ventricular Arrythmia | 221 | 204 |
| M | M.Bue | Arterial Sclerosis of the Legs | 361 | 230 |
| F | M.Bi. | Coronary Insufficiency | 322 | 247 |
| F | A.Ec. | Coronary Insufficiency | 243 | 266 |
| M | R.As. | Bronchial Asthma | 287 | 223 |
| F | E.As. | No Illness | 250 | 233 |
| M | O.En. | Cerebral Sclerosis Arterial Sclerosis of the Leg Arteries | 219 | 230 |
| M | G.Fr. | Coronary Insufficiency | 184 | 163 |
| M | M.Ge. | Arterial Sclerosis | 222 | 206 |
| F | R.Ge. | Arterial Sclerosis | 372 | 256 |

Significance: 98% (2d–0.02) average decrease approx. 16%

TABLE III

| Sex | Name | Illness | Cholesterol Level Prior to Treatment | After a Three-Month Treatment |
|---|---|---|---|---|
| M | M.Bue | Arterial Sclerosis of the Legs | 361 | 242 |
| M | R.As. | Bronchial Asthma | 287 | 284 |
| F | M.Gr. | Overfunction of the Thyroid Gland | 419 | 406 |
| F | A.Gu. | No Illness | 250 | 267 |
| F | J.Ma. | Arterial Sclerosis | 334 | 234 |
| M | R.M.e | No Illness | 339 | 348 |
| F | N.Ho. | Coronary Insufficiency | 328 | 340 |
| F | L.Ho. | Migrane | 288 | 312 |
| M | W.N. | No Illness | 220 | 183 |
| F | Th. Mue. | No Illness | 274 | 238 |
| F | M.Mue | No Illness | 335 | 243 |
| F | Th.M. | Heart Muscle Damage | 274 | 238 |
| F | M.Mo. | No Illness | 303 | 293 |
| F | R.Mu. | Wilson Black | 306 | 284 |
| M | L.Pa. | Arterial Sclerosis | 523 | 423 |
| F | Ma.Wi. | No Illness | 298 | 249 |
| M | Dr. T. | Hypertonia | 365 | 405 |
| F | R.Wa. | Anemia | 288 | 285 |
| F | E.W. | No Illness | 294 | 274 |

Significance: approx. 95%(2d–0.05)-average decrease approx.9.6%

In summary the test results show that:
1. Oral administration of the polypeptide of this invention is possible and the proteolysis remains at the short-chain polypeptide level even when trypsin or propane are used for the enzymatic proteolysis.
2. The cholesterol level reduction in the tested patients is significant.

The following table shows clinical test results on the increase of the 17 keto-steroid elimination of patients receiving the indicated dosages of the polypeptide of this invention for the indicated duration and also showing the increased elimination when the polypeptide of this invention is used in combination with "testoviron" which is a brand name for testosterone. The polypeptide used in the oral doses was prepared according to Example 1.

TABLE IV

| Name | Age | 17 keto-steroid elimination prior to treatment (mg./24 h) | 17 keto steroid elimination after a one-week intake of 100 mg. polypeptide per day (oral) (mg./24 h) | 17 keto-steroid elimination after a one-week intake of 100 mg. polypeptide per day (oral) plus 10 mg. testoviron* per day (oral) (mg./24/ h) | 17 keto-steroid elimination after a one-week treatment with 10 mg. testoviron* per day (oral) (mg./24 h) |
|---|---|---|---|---|---|
| W.G. | 65 | 7.6 | 13.8 | 11.3 | 10.7 |
| H.M. | 65 | 7.7 | — | 18.4 | 11.5 |
| B.G. | 75 | 8.3 | 19.0 | — | 12.6 |

*Brand Name for Testosterone

The results compiled in Table IV show that the increase in 17 keto-steroid elimination achieved by means of the polypeptide of this invention is significantly greater than the increase achieved through testosterone or even with a combined testosterone-polypeptide dosage. The daily elimination is double. It will be noted that the patients treated were elderly and that the polypeptide is exceptionally suited to activate hormone production in older persons. The invention thus provides treatment to increase 17 keto-steroid elimination in older persons over a long period of time in a physiologically unobjectionable manner.

While pepsin, trypsin and papain are preferred enzymes for the proteolysis breakdown of the reticuloendotelial tissue, it is surprising that proteolysis even when using such active enzymes as trypsin or papain does not progress to amino acid but remains at the short-chain level of the polypeptide of this invention. Thus, the polypeptide is suitable for oral administration because these enzymes in the stomach will not break down the polypeptide.

The process of separation of the polypeptide can take place by means of alkaline metal salts, alkaline-earth metal salts, ammonia salts or aluminum salts or other separation processes, for example water soluble organic solvents or partial water soluble solvents such as phenol may be used. The concentrates obtained by a salting-out process are particularly suitable for oral administration but the polypeptide can be used parenterally in which case an additional purification step is desirable. Suitable purification for parenteral usage can be effected through isoelectric precipitation, column chromatography with anion or cation exchange resins, cellulose, silica gel, aluminum oxide, or other absorbents or through electrophoresis.

From the above descriptions, it will be understood that this invention produces a physiologically active polypeptide by enzymatic proteolysis of animal organs which includes subjecting a fresh minced animal organ rich in reticulo-endotelial tissue to the action of a proteolytic enzyme at a temperature not substantially exceeding 45° C, separating the resulting proteolyzed liquid from solid matter and then either precipitating a polypeptide from the liquid by addition of water soluble salts such as alkaline metal salts, alkaline-earth metal salts, aluminum salts, ammonia salts, or by means of a partly water soluble organic solvent, separating the solvent layer from the aqueous layer, removing the organic solvent from the solvent layer by means of a water insoluble solvent for the organic solvent, and then recovering the purified polypeptide from the residual extracted layer. The preferred precipitating salt is sodium chloride, the preferred water soluble organic solvent is phenol and the preferred water insoluble solvent for the phenol is ether. The polypeptide has an electrolytic point at a pH of about 5.5, a molecular weight of less than 5,000, an Rf value in Partridge solution between 0.5 and 0.6, is brown-colored, has a violet ninhydrin reaction, is soluble in water containing phenol and insoluble in ether and has a relatively short-chain molecule. The polypeptide will not breakdown in the stomach and can be administered orally.

I claim as my invention:
1. The method of preparing a physiologically active polypeptide effective for lowering cholesterol levels in blood and increasing the 17-keto-steroid elimination when administered orally or parenterally to human patients which comprises adding water to minced animal organs rich in reticulo-endotelial tissue, stirring a proteolytic enzyme into the mass, maintaining the mixture at a temperature, from about 40° C to not substantially above 45° C for at least 5 hours and not more than about 72 hours, filtering the solution from the solids, and separating a polypeptide from the filtrate having a molecular weight less than 5,000, an isoelectric point at a pH of about 5.5 and an Rf value between 0.5 and 0.6 in Partridge solution.

2. The method of claim 1 wherein the proteolytic enzyme is selected from the group consisting of pepsin, trypsin and papain.

3. The method of claim 1 wherein the polypeptide is separated from the filtrate by the addition of a water soluble salt selected from the group consisting of alkaline metal salts, alkaline-earth metal salts, aluminum salts and ammonia salts.

4. The method of claim 1 wherein the polypeptide is separated from the filtrate with a partly water soluble organic solvent and is separated from the solvent by extraction with a water insoluble solvent for the organic solvent.

5. The method of claim 4 wherein the water soluble organic solvent is phenol and the water insoluble solvent for the phenol is ether.

6. The method of claim 1 wherein the animal organs are selected from the group consisting of animal spleens, lymph glands, and bone marrow.

7. The physiologically active short chain polypeptide obtained by the method of claim 1 and consisting of the following 17 amino acids:
Lysine
Histidine
Arginene
Asparagine acid
Threonine
Serine
Glutamic acid
Proline
Glycine
Alanine
Cysteine
Valine
Methionine
Isoleucine
Leucine
Tryosine
Phenylalanine.

* * * * *